(12) United States Patent
Arima

(10) Patent No.: US 11,538,187 B2
(45) Date of Patent: Dec. 27, 2022

(54) RADIOGRAPHIC SYSTEM, RADIOGRAPHIC METHOD, AND STORAGE MEDIUM

(71) Applicant: CANON KABUSHIKI KAISHA, Tokyo (JP)

(72) Inventor: Keisuke Arima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/561,768

(22) Filed: Sep. 5, 2019

(65) Prior Publication Data

US 2020/0082569 A1 Mar. 12, 2020

(30) Foreign Application Priority Data

Sep. 11, 2018 (JP) .............................. JP2018-169616

(51) Int. Cl.
*G06T 7/80* (2017.01)
*G16H 30/40* (2018.01)
*G06T 7/00* (2017.01)

(52) U.S. Cl.
CPC .............. *G06T 7/80* (2017.01); *G06T 7/0012* (2013.01); *G16H 30/40* (2018.01); *G06T 2207/10116* (2013.01)

(58) Field of Classification Search
CPC ...................... G06T 7/80; G06T 7/0012; G06T 2207/10116; G16H 30/40; G16H 30/20; G16H 40/63; A61B 6/44; A61B 6/40; A61B 6/54
See application file for complete search history.

(56) References Cited

U.S. PATENT DOCUMENTS

| 8,924,864 B2 * | 12/2014 | Mariotti | G16H 30/40 |
| | | | 715/753 |
| 10,685,088 B2 * | 6/2020 | Ohashi | A61B 6/566 |
| 10,733,566 B1 * | 8/2020 | Chan | G06N 20/00 |
| 2011/0311026 A1 * | 12/2011 | Lalena | A61B 6/545 |
| | | | 378/98.5 |
| 2013/0090946 A1 * | 4/2013 | Foo | G16H 30/20 |
| | | | 705/3 |

(Continued)

FOREIGN PATENT DOCUMENTS

| JP | 2009-070074 A | 4/2009 |
| JP | 2011-050584 A | 3/2011 |

(Continued)

*Primary Examiner* — Emily C Terrell
*Assistant Examiner* — Molly Wilburn
(74) *Attorney, Agent, or Firm* — Canon U.S.A., Inc. IP Division

(57) ABSTRACT

A radiographic system includes a storage unit configured to store a plurality of imaging methods in association with a plurality of imaging protocols, a determination unit configured to determine whether an imaging method of an imaging protocol associated with an examination order matches at least one of the plurality of imaging methods stored in the storage unit, and an image processing unit configured to apply, in a case where the determination unit determines that the imaging method matches at least one imaging method, an image processing condition of an imaging protocol corresponding to the at least one imaging method to a radiographic image captured based on the imaging protocol associated with the examination order.

10 Claims, 6 Drawing Sheets

(56) References Cited

U.S. PATENT DOCUMENTS

| | | | | |
|---|---|---|---|---|
| 2013/0129165 A1* | 5/2013 | Dekel | ................... | G16H 30/40 |
| | | | | 382/128 |
| 2014/0112447 A1* | 4/2014 | Semba | .................. | A61B 6/545 |
| | | | | 378/98 |
| 2014/0114673 A1* | 4/2014 | Hu | ........................ | G16H 15/00 |
| | | | | 705/2 |
| 2016/0133012 A1* | 5/2016 | Miyazawa | .............. | G06T 11/60 |
| | | | | 382/132 |
| 2016/0210437 A1* | 7/2016 | Padmani | ............ | G06Q 10/0631 |
| 2017/0163869 A1* | 6/2017 | Semba | ................ | H04N 5/23293 |
| 2018/0301216 A1* | 10/2018 | Nakamura | ........... | A61B 5/7425 |
| 2019/0362203 A1* | 11/2019 | Sung | ...................... | B41J 11/003 |
| 2019/0385299 A1* | 12/2019 | Song | .................... | G06T 7/0012 |

FOREIGN PATENT DOCUMENTS

| | | |
|---|---|---|
| JP | 2014-83123 A | 5/2014 |
| JP | 2017-099758 A | 6/2017 |

\* cited by examiner

FIG.3A

| PROTOCOL ID | PROTOCOL NAME | IMAGING METHOD ID | IMAGING CONDITION ID | IMAGE PROCESSING ID |
|---|---|---|---|---|
| P1 | CHEST PA | T1 | Ex1 | IP1 |
| P2 | CHEST AP | T2 | Ex1 | IP2 |
| P3 | PNEUMOCONIOSIS | T1 | Ex1 | IP3 |
| P4 | CHEST RL | T3 | Ex2 | IP4 |
| P5 | CHEST LL | T4 | Ex2 | IP5 |
| P6 | ABDOMEN PA | T5 | Ex3 | IP1 |
| P7 | ABDOMEN AP | T6 | Ex3 | IP2 |
| P8 | ABDOMEN RL | T7 | Ex4 | IP3 |
| P9 | ABDOMEN LL | T8 | Ex4 | IP4 |
| P10 | CHEST PA | T9 | Ex5 | IP5 |

FIG.3B

| IMAGING METHOD ID | IMAGED REGION | IMAGING DIRECTION | IMAGING ATTITUDE |
|---|---|---|---|
| T1 | CHEST | Posterior/Anterior | STANDING |
| T2 | CHEST | Anterior/Posterior | STANDING |
| T3 | CHEST | Anterior/Posterior | STANDING |
| T4 | CHEST | Left Lateral | STANDING |
| T5 | ABDOMEN | Posterior/Anterior | STANDING |
| T6 | ABDOMEN | Anterior/Posterior | STANDING |
| T7 | ABDOMEN | Right Lateral | STANDING |
| T8 | ABDOMEN | Left Lateral | STANDING |
| T9 | CHEST | Posterior/Anterior | LYING |

FIG.3C

| IMAGING CONDITION ID | TUBE CURRENT | TUBE VOLTAGE | IRRADIATION TIME | EIT |
|---|---|---|---|---|
| Ex1 | I1 | E1 | T1 | EIT1 |
| Ex2 | I2 | E2 | T2 | EIT2 |
| Ex3 | I3 | E3 | T3 | EIT3 |
| Ex4 | I4 | E4 | T4 | EIT4 |
| Ex5 | I5 | E5 | T5 | EIT5 |

FIG.3D

| IMAGE PROCESSING ID | LUMINANCE | CONTRAST | EMPHASIS PROCESSING |
|---|---|---|---|
| IP1 | B1 | C1 | En1 |
| IP2 | B2 | C2 | En2 |
| IP3 | B3 | C3 | En3 |
| IP4 | B4 | C4 | En4 |
| IP5 | B5 | C5 | En5 |

RADIOGRAPHIC SYSTEM, RADIOGRAPHIC METHOD, AND STORAGE MEDIUM

BACKGROUND

Field of the Disclosure

The present disclosure relates to a radiographic system that applies a radiation to an examinee and captures a radiographic image, and to a radiographic method and a storage medium.

Description of the Related Art

A radiographic apparatus applies a radiation (e.g., X-ray) to an examinee, and detects intensity distribution of the radiation passed through the examinee, thereby capturing a radiographic image of an object.

In an examination using a radiation (radiographic examination), examination information including an imaging region and an imaging method is generally set by a physician. Radiographic imaging is then performed by the radiographic apparatus based on the set examination information.

Depending on the performed examination, the radiographic apparatus performs different image processing on one image to acquire a plurality of radiographic images. For example, in chest checkup, copying processing is performed on a chest image acquired by one-time imaging, and image processing for general chest diagnosis and image processing for pneumoconiosis diagnosis are performed to acquire two radiographic images in some cases. Further, the radiographic apparatus may acquire a common radiographic image in which a radiation-permeable part is black and a radiation-impermeable part is white, and a reverse radiographic image in which black and white are reversed, in some cases. Japanese Patent Application Laid-Open No. 2014-83123 discusses a method of copying a radiographic image.

SUMMARY

An examination order set to the radiographic imaging does not include a copying instruction of the radiographic image. Therefore, it is required for a medical technician performing the radiographic imaging to provide the copying instruction and perform image processing on the radiographic image for each imaging.

The present invention is directed to a radiographic system, a radiographic method, and a storage medium that each make it possible to appropriately perform image processing based on an imaging protocol associated with an examination order, thereby effectively performing radiographic imaging.

According to an aspect of the present invention, a radiographic system includes a storage unit configured to store a plurality of imaging methods in association with a plurality of imaging protocols, a determination unit configured to determine whether an imaging method of an imaging protocol associated with an examination order matches at least one of the plurality of imaging methods stored in the storage unit, and an image processing unit configured to apply, in a case where the determination unit determines that the imaging method matches at least one imaging method, an image processing condition of an imaging protocol corresponding to the at least one imaging method to a radiographic image captured based on the imaging protocol associated with the examination order.

Further features of the present invention will become apparent from the following description of exemplary embodiments with reference to the attached drawings.

BRIEF DESCRIPTION OF THE DRAWINGS

FIGS. 3A to 3D are diagrams each illustrating a configuration of an imaging protocol table in the radiographic system according to the exemplary embodiment.

DESCRIPTION OF THE EMBODIMENTS

Some preferred exemplary embodiments of the present invention are described below with reference to accompanying drawings.

Figure 1:
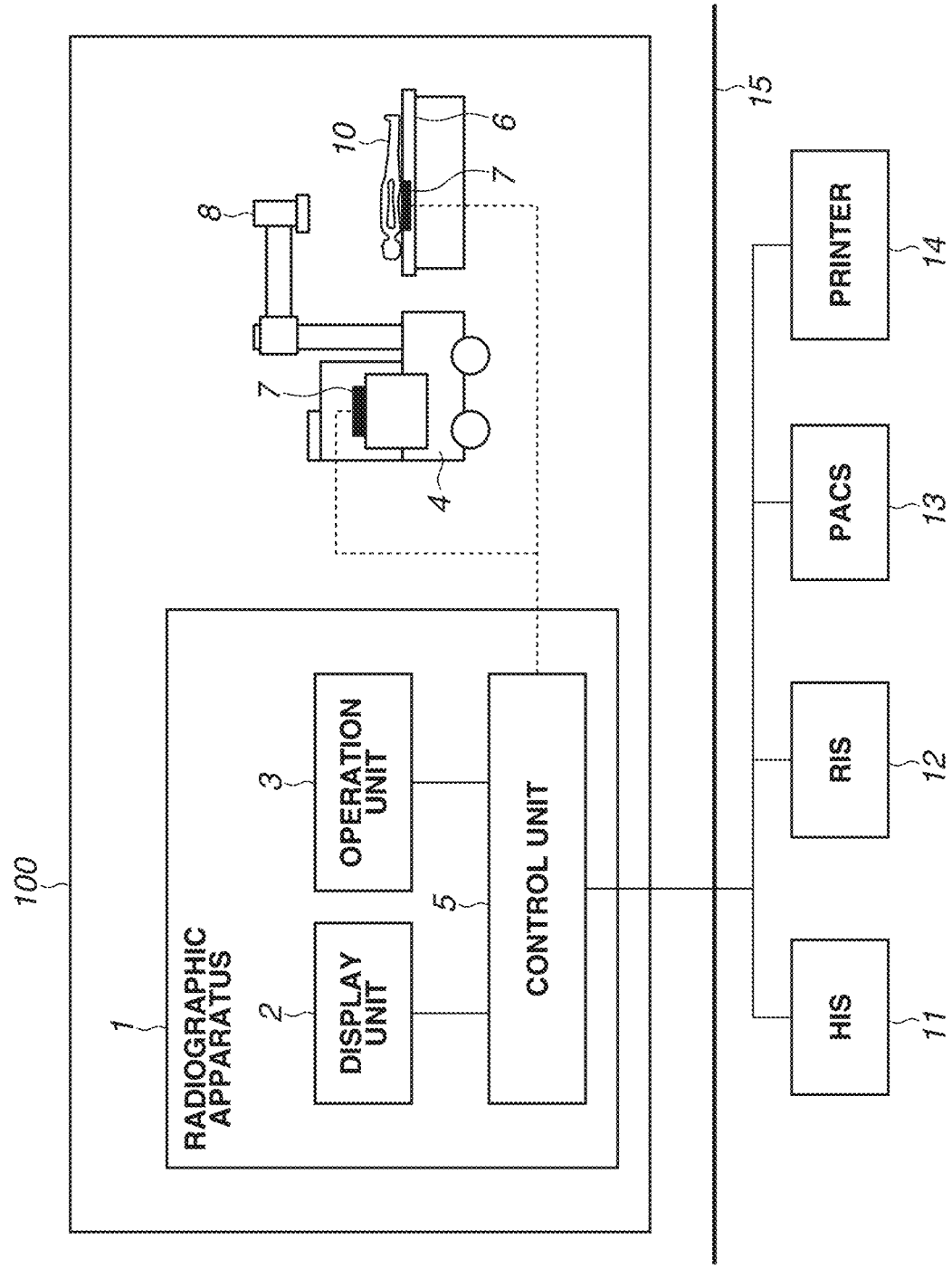
FIG. 1 is a block diagram illustrating an entire configuration of a radiographic system according to an exemplary embodiment.

A first exemplary embodiment of the present invention is described with reference to FIG. 1. FIG. 1 is a diagram illustrating a configuration example of a radiographic system. As illustrated in FIG. 1, the radiographic system includes a radiographic apparatus 1 and a hospital information system (HIS) 11 that mainly manages progress of an examination.

The radiographic system further includes a radiology information system (RIS) 12 that transmits an examination order to the radiographic apparatus 1. Further, the radiographic system is connected to a picture archiving and communication system (PACS) 13 that manages a radiographic image, and to a printer 14 that prints and outputs the radiographic image.

The HIS 11 is a hospital management system, and includes a server that manages progress of an examination and accounting information. When radiographic imaging is performed, an operator inputs an examination instruction from a terminal (input unit) of the HIS 11. The HIS 11 transmits request information to a radiological department of the hospital that is a request destination of the radiographic imaging. The request information is called an examination order. The examination order includes a department name of the operator (client), an examination identification (ID), an examination item, and personal data of an examinee (subject).

When receiving the examination order through the RIS 12, the radiological department adds, as an imaging protocol, imaging information (e.g., imaged region information, imaging direction information, and procedure information) relating to the radiographic imaging to the examination order, and transmits the resultant examination order to the radiographic apparatus 1. The radiographic apparatus 1 performs radiographic imaging based on the received examination order. The radiographic apparatus 1 acquires a captured radiographic image, generates examination information in which the radiographic image and the examination order are associated with each other, and outputs the examination information together with the radiographic image.

The PACS 13 is a server managing the radiographic image. An image inspection work, detailed post-processing, and a diagnosis work of the radiographic image are performed with use of a high-definition monitor connected to the PACS 13. As described above, the radiographic image acquired by the radiographic apparatus 1 is transmitted to the PACS 13.

Execution information (e.g., image ID and imaging date) of the examination by the radiographic apparatus 1 is transmitted to the HIS 11. The execution information transmitted to the HIS 11 is also used for accounting processing after the examination, in addition to the progress management of the examination.

The radiographic apparatus 1, the HIS 11, the RIS 12, the PACS 13, and the printer 14 are connected to one another via a network 15, such as a local area network (LAN) and a wide area network (WAN).

Each of these apparatuses includes one or more computers. Each of the computers is provided with, for example, a main control unit (e.g., a central processing unit (CPU)), and a storage unit (e.g., a read-only memory (ROM), and a random access memory (RAM)). Each of the computers may be provided with a communication unit (e.g., a network card), and an input/output unit (e.g., a keyboard, a display, and a touch panel). These configuration units are electrically connected via, for example, a bus, and are controlled when the main control unit executes a program stored in the storage unit.

As illustrated in FIG. 1, the radiographic apparatus 1 that performs the radiographic imaging is placed in an imaging room 100. Further, a radiation generation apparatus 4 that generates a radiation, a radiation detection apparatus 7 that detects a radiation passed through an examinee 10 to capture a radiographic image, and an imaging table 6 that holds the radiation detection apparatus 7 are placed in the imaging room 100.

The radiographic apparatus 1 includes a display unit 2 that displays the radiographic image and various kinds of information, an operation unit 3 operated by the operator, and a control unit 5 that controls each component described above.

The radiation generation apparatus 4 sets an imaging condition of the radiation in a radiation generation unit 8, and controls generation of the radiation from the radiation generation unit 8. The radiation generation unit 8 functions as a radiation source that generates the radiation. The radiation generation unit 8 is realized by, for example, a radiation tube bulb (e.g., X-ray tube), and applies a radiation to the examinee 10 (e.g., specific region of examinee).

The radiation generation unit 8 can apply the radiation to a desired irradiation range. A diaphragm (not illustrated) that shields the radiation is disposed on an irradiation surface of the radiation generation unit 8. The operator can adjust the irradiation range of the radiation emitted from the radiation generation unit 8 by controlling the diaphragm that shields the radiation.

The radiographic system includes the radiation detection apparatus 7 that detects the radiation emitted from the radiation generation unit 8. The radiation detection apparatus 7 detects the radiation passed through the examinee 10, and outputs a radiographic image corresponding to the detected radiation. The radiographic image is also referred to as radiation data.

Specifically, the radiation detection apparatus 7 detects the radiation passed through the examinee 10, as charges corresponding to a dosage of the passed radiation. For example, in the radiation detection apparatus 7, a direct-conversion sensor, such as amorphous selenium (a-Se) that directly converts a radiation into charges or an indirect-conversion sensor that uses a scintillator, such as cesium iodide (CsI), and a photoelectric conversion device, such as amorphous silicon (a-Si), is used.

The radiation detection apparatus 7 is a portable cassette radiation detection apparatus, and is carried together with the radiation generation apparatus 4 to the imaging room 100 in which the examination is performed. One of radiation detection apparatuses different in size is selected depending on a size of the examinee and an imaged region, and the radiographic imaging is performed. In the embodiment, the radiation detection apparatus 7 disposed on the imaging table 6 is used in the radiographic imaging.

The radiation detection apparatus 7 performs A/D conversion on the detected charges to generate a radiographic image, and accumulates the radiographic image in a storage unit (not illustrated). The radiation detection apparatus 7 can provide image information (e.g., image ID, imaging date, and transfer condition of the radiographic image) to the radiographic image, and transfer the image information together with the radiographic image to the radiographic apparatus 1.

The display unit 2 is realized by, for example, a liquid crystal display, and displays various kinds of information to the operator (e.g., radiographer and physician). The operation unit 3 includes a mouse and an operation icon, and various kinds of instructions from the operator are input to the components. The display unit 2 and the operation unit 3 may be integrated as a touch panel.

The control unit 5 of the radiographic apparatus 1 is connected to the radiation detection apparatus 7 via a wireless LAN. The radiographic image, a control signal, and the like are transmitted/received between the control unit 5 and the radiation detection apparatus 7. In other words, the radiographic image stored in the radiation detection apparatus 7 by the radiographic imaging is output (transferred) to the control unit 5 via the wireless LAN.

The radiographic apparatus 1 includes the control unit 5 that performs image processing on the radiographic image output from the radiation detection apparatus 7 to generate an image. The control unit 5 has an application function operated on a computer. The control unit 5 controls operation of the radiation detection apparatus 7, outputs the radiographic image to the display unit 2, and outputs a graphical user interface (GUI).

Figure 2:
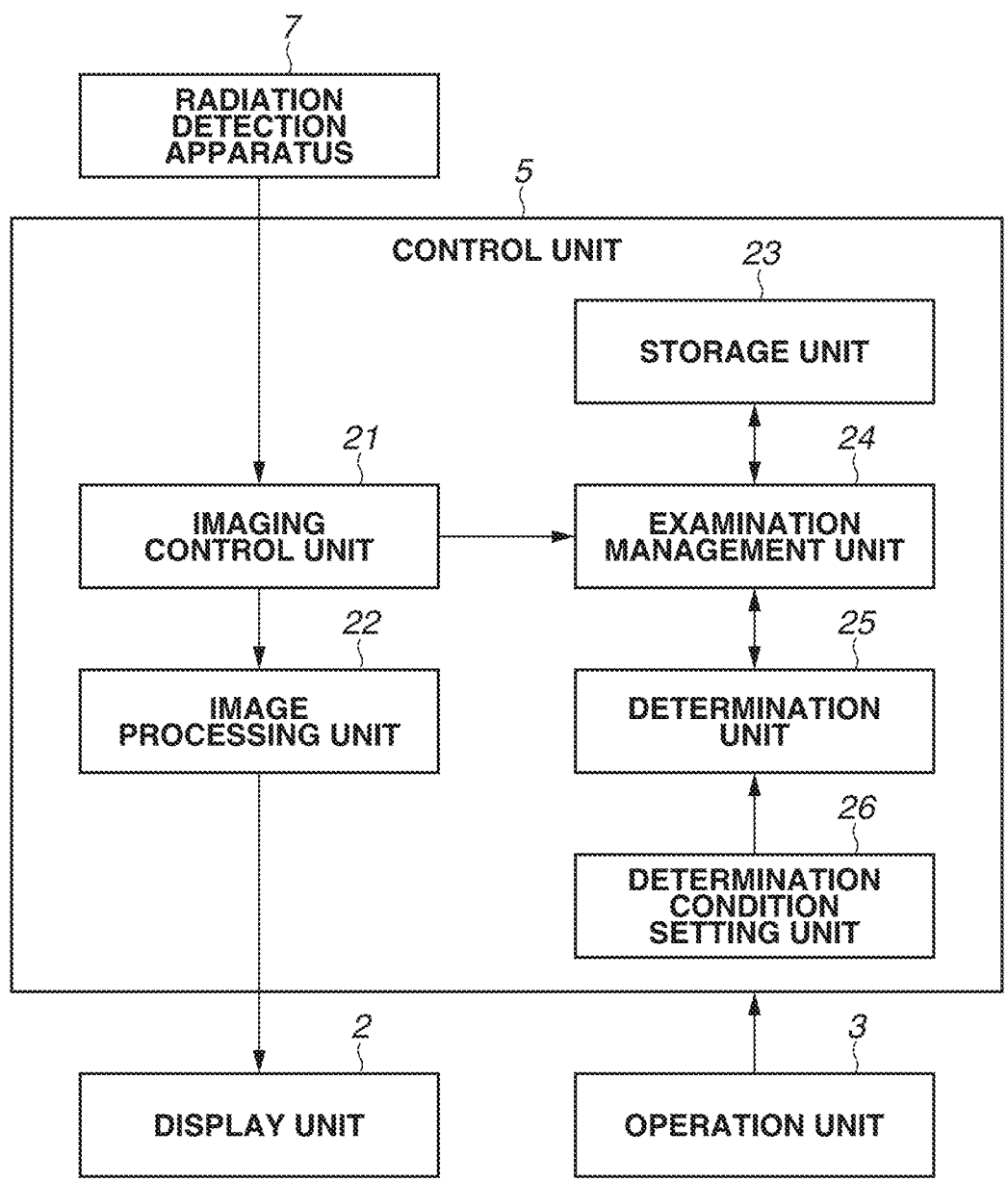
FIG. 2 is a block diagram illustrating a configuration of a control unit in the radiographic system according to the exemplary embodiment.

The control unit 5 of the radiographic system according to the present exemplary embodiment is described in detail with reference to FIG. 2. The control unit 5 includes an imaging control unit 21, an image processing unit 22, and a storage unit 23. The imaging control unit 21 performs imaging control of the radiation detection apparatus 7. The image processing unit 22 performs image processing on the radiographic image acquired by imaging. The storage unit 23 stores the radiographic image output from the radiation detection apparatus 7, and various kinds of information, such as the examination order, the imaging protocol, and the imaging method. The control unit 5 further includes an examination management unit 24, a determination unit 25, and a determination condition setting unit 26. The examination management unit 24 manages the examination information in which the radiographic image and the examination order are associated with each other. The determination unit 25 determines whether the imaging method same as the imaging method of the imaging protocol associated with the examination order has been stored in the storage unit 23. The determination condition setting unit 26 sets a determination condition used in the determination unit 25. The determination unit 25 determines whether the imaging method of the imaging protocol associated with the examination order matches any of a plurality of imaging methods stored in the storage unit 23.

The storage unit 23 stores the examination information, the imaging protocol, and the imaging methods that are managed by the examination management unit 24, the radiographic image output from the radiation detection apparatus 7, and various kinds of information required for examination management. The storage unit 23 further stores the imaging protocol associated with the examination order, together with identification information for identifying the imaging protocol.

The examination management unit 24 manages the imaging protocol associated with the examination order. In the imaging protocol, the imaging method, the imaging condition, the image processing condition, and the like are defined. The examination management unit 24 can associate examinee information with the imaging protocol, the examinee information and the imaging protocol having been input from the operation unit 3, to create new examination information, in a case, for example, where the radiographic apparatus 1 generates the examination information. In contrast, the examination management unit 24 extracts the imaging protocol stored in the storage unit 23 with use of the identification information on the imaging protocol associated with the received examination order, in a case where an examination is requested from the RIS 12. The examination management unit 24 associates the extracted imaging protocol with the examination order, thereby creating new examination information. The newly-created examination information is stored in the storage unit 23.

The imaging control unit 21 transmits, to the radiation detection apparatus 7, a transfer request signal requesting transfer of the radiographic image accumulated in the radiation detection apparatus 7, and receives the radiographic image from the radiation detection apparatus 7. The imaging control unit 21 manages the received radiographic image together with radiation detection apparatus information relating to the radiation detection apparatus 7. The imaging control unit 21 further associates the radiographic image with the examination information and the imaging protocol that are managed by the examination management unit 24.

The image processing unit 22 performs image processing on the radiographic image with use of the imaging protocol and the image information acquired by the imaging control unit 21. The image-processed radiographic image is displayed on the display unit 2. The image processing unit 22 performs the image processing to adjust the image itself, for example, luminance/contrast adjustment. The image processing unit 22 can also perform processing such as extraction and annotation on the adjusted radiographic image.

The determination unit 25 determines whether the imaging protocol that has been associated with the examination order and performed by the radiation detection apparatus 7, belongs to the imaging method group same as the imaging protocol stored in the storage unit 23. The imaging protocol stored in the storage unit 23 is managed by the examination management unit 24. The imaging protocol stored in the storage unit 23 is, for example, the imaging protocol of the last imaging. In other words, the determination unit 25 determines whether the imaging protocol of the radiographic imaging that has been associated with the examination order and performed by the radiation detection apparatus 7, belongs to the imaging method group same as the imaging protocol managed by the examination management unit 24.

The imaging protocol includes the imaging method (e.g., imaged region, imaging direction, and imaging attitude) and the imaging condition (e.g., tube voltage, tube current, irradiation time) set by the radiation generation apparatus 4. The storage unit 23 stores the imaging method and the imaging condition as the imaging protocol. The determination unit 25 may compare the imaging method used in the imaging protocol for the radiographic imaging that has been associated with the examination order and performed by the radiation detection apparatus 7, with the imaging methods of the plurality of imaging protocols in the same examination, thereby determining whether these imaging methods belong to the same imaging method group. In other words, the determination unit 25 determines whether the imaging method of the imaging protocol of the radiographic imaging that has been associated with the examination order and performed by the radiation detection apparatus 7, is the same as the imaging method of the imaging protocol in the same examination.

FIGS. 3A to 3D are diagrams illustrating determination of the same imaging method group by the determination unit 25 according to the present exemplary embodiment. FIG. 3A illustrates an imaging protocol table stored in the storage unit 23. The imaging protocol table associates the various kinds of information, such as the imaging method, the imaging condition, and the image processing condition, with the imaging protocol. The imaging protocol table holds identification information (ID) of the imaging protocol and an imaging protocol name. The imaging protocol table further holds identification information (ID) to extract the imaging method, the imaging condition, and the image processing condition. In the imaging protocol table, the same imaging method ID of the imaging protocol indicates the same imaging method. For example, in FIG. 3A, the imaging protocol IDs P1 and P3 have the same imaging method ID T1. Therefore, the imaging methods in the imaging protocols P1 and P3 are the same.

Further, in the imaging protocol table, the same imaging condition ID of the imaging protocol indicates the same imaging condition. For example, in FIG. 3A, the imaging protocol IDs P1, P2 and P3 have the same imaging condition ID EX1. Therefore, the imaging conditions in the imaging protocols P1, P2 and P3 are the same. Likewise, the imaging protocol IDs P4 and P5 have the same imaging condition ID EX2. Therefore, the imaging conditions in the imaging protocols P4 and P5 are the same.

Moreover, in the imaging protocol table, the same image processing condition ID of the imaging protocol indicates the same image processing condition. For example, in FIG. 3A, the imaging protocol IDs P1 and P6 have the same image processing condition ID IP1. Therefore, the image processing conditions in the imaging protocols P1 and P6 are the same. Likewise, the imaging protocol IDs P2 and P7 have the same image processing condition ID IP2. Therefore, the image processing conditions in the imaging protocols P2 and P7 are the same.

FIG. 3B illustrates an imaging method table in which the imaging method IDs of the imaging protocols illustrated in FIG. 3A are classified. The imaging method table holds the imaging method IDs. The imaging method table further holds imaging information on the examinee in the radiographic imaging, such as the imaged region, the imaging direction, and the imaging attitude. A distance between the radiation generation unit 8 and the radiation detection apparatus 7, and a body thickness of the examinee 10 may be held as the information on the imaging method.

In the imaging method table, when at least the imaged region and the imaging method are the same between the imaging method IDs, the imaging methods are regarded as the same method of imaging. For example, in FIG. 3B, the imaged region is a chest and the imaging direction is Posterior/Anterior in the imaging method of each of the imaging method IDs T1 and T9. Thus, the imaged region and the imaging direction are the same between the imaging method IDs T1 and T9. Therefore, the imaging methods in the imaging method IDs T1 and T9 are the same.

The determination unit 25 determines, based on the imaging protocol table, whether there is the imaging protocol belonging to the imaging method group same as the imaging protocol that has been associated with the examination order and performed by the radiation detection apparatus 7.

As illustrated in FIG. 3A, in the imaging protocol table, the same imaging method ID of the imaging protocol is regarded as the same imaging method. The determination unit 25 determines, based on the imaging protocol table, whether there is the imaging protocol belonging to the imaging method group same as the imaging protocol that has been associated with the examination order and performed by the radiation detection apparatus 7. For example, in FIG. 3A, the imaging protocol P1 for a chest PA and the imaging protocol P3 for pneumoconiosis have the same imaging method ID T1. The same imaging method ID indicates the imaging protocol in which the same region is imaged from the same direction.

Pneumoconiosis processing, which is image processing of the imaging protocol P3 for pneumoconiosis, is processing that applies image processing predetermined for pneumoconiosis to generate a radiographic image, aside from the radiographic image subjected to normal image processing. Specifically, the pneumoconiosis processing is different from the normal image processing apparatus in image processing parameters relating to gradation conversion for each frequency component, luminance, contrast, edge enhancement, and noise reduction.

In this case, the imaging protocol table illustrated in FIG. 3A holds the imaging protocol that is stored in the storage unit 23 and is managed by the examination management unit 24, or the imaging protocol associated with the examination order in the same examination. The determination unit 25 determines whether the imaging method of the imaging protocol associated with the examination order of the examinee matches the imaging method in the imaging protocol table. In other words, the determination unit 25 determines whether the imaging protocol associated with the examination order of the examinee belongs to the same imaging method group of the imaging protocol table.

In a case where the imaging method included in the examination order of the examinee matches the imaging method in the imaging protocol table, the image processing unit 22 performs, on the radiographic image, the image processing same as the image processing of the imaging method in the imaging protocol table, thereby generating a resultant radiographic image.

For example, when the imaging method ID of the imaging protocol associated with a new examination order is T1, the determination unit 25 determines that the imaging method of the imaging protocol associated with the examination order of the examinee matches the imaging method ID T1 in the imaging protocol table. The image processing unit 22 performs, on the radiographic image, the image processing (i.e., image processing for chest PA and processing for pneumoconiosis) of the imaging method in the imaging protocol table, thereby generating resultant radiographic images.

In this example, the imaging method ID T2 and the imaging method ID T9 illustrated in FIG. 9B are determined as the same imaging method even though, for example, the imaging attitudes are not the same. In other words, the imaging methods are determined as the same imaging method when the imaging methods at least have the same imaged region and the same imaging direction. The determination condition setting unit 26 can sets the determination condition in the determination unit 25. The determination condition setting unit 26 can add the imaging attitude to the determination condition in the determination unit 25, in addition to the imaged region and the imaging direction. Specifically, when the imaging protocol table holds the imaging protocol in which the imaged region, the imaging direction, and the imaging attitude are the same as the imaged region, the imaging direction, and the imaging attitude of the imaging protocol associated with the examination order of the examinee, the determination unit 25 determines as the same imaging method. In a case where the imaged region, the imaging direction, and the imaging attitude of the imaging protocol associated with the examination order of the examinee respectively matches with the imaged region, the imaging direction, and the imaging attitude in the imaging protocol table, the image processing unit 22 performs, on the radiographic image, the image processing same as the image processing of the imaging method in the imaging protocol table, thereby generating a resultant radiographic image.

FIG. 3C illustrates an imaging condition table stored in the storage unit 23. The imaging condition table holds identification information (ID) of the imaging condition. The imaging condition table further holds the imaging condition, such as exposure index target (EIT), relating to the radiation generated by the radiation generation apparatus 4. When the imaging protocol table holds the imaging protocol in which the imaged region, the imaging direction, and the imaging condition are the same as the imaged region, the imaging direction, and the imaging condition of the imaging protocol associated with the examination order of the examinee, the determination unit 25 determines that the imaging methods are the same. In a case where the imaged region, the imaging direction, and the imaging condition of the imaging protocol associated with the examination order of the examinee respectively matches with the imaged region, the imaging direction, and the imaging condition in the imaging protocol table, the image processing unit 22 performs, on the radiographic image, the image processing same as the image processing of the imaging method in the imaging protocol table, thereby generating a resultant radiographic image.

As illustrated in FIG. 3A, in addition to the imaging method ID, the imaging condition IDs are the same between the imaging protocol P1 for the chest PA and the imaging protocol P3 for the pneumoconiosis. The same imaging method ID and the same imaging condition ID indicate that the imaging is performed with the same imaging method while the radiation generation apparatus 4 emits the same radiation. The determination unit 25 determines that these imaging protocols belong to the same imaging method group. FIG. 3C illustrates the tube current, the tube voltage, the irradiation time, and the parameter of the EIT as the imaging condition. However, these parameters are not necessarily required. When the tube current, the tube voltage, and the irradiation time of the radiation generation apparatus 4 match, the determination unit 25 may determine that the imaging conditions are the same. Alternatively, when the tube current and the tube voltage of the radiation generation apparatus 4 match, the determination unit 25 may determine that the imaging conditions are the same. The determination condition setting unit 26 may set the determination condition relating to the imaging condition in the determination unit 25. The determination unit 25 determines that the imaging conditions are the same when the imaging condition table holds the imaging condition same as the imaging condition of the imaging protocol associated with the examination order of the examinee.

FIG. 3D illustrates an image processing condition table stored in the storage unit 23. The image processing condition table holds the identification information (ID) of the image processing condition. The image processing condition table further holds the image processing condition such as a parameter for image processing (e.g., luminance, contrast, and enhancement processing) performed on the captured image. The determination condition setting unit 26 can add the image processing condition to the determination condition in the determination unit 25, in addition to the imaged region and the imaging direction.

As described above, the determination condition setting unit 26 can optionally set the determination condition in the determination unit 25, and can set the determination parameter (e.g., imaging attitude and imaging condition), in addition to the imaged region and the imaging direction that are required for determination of the imaging method by the determination unit 25.

Figure 4:
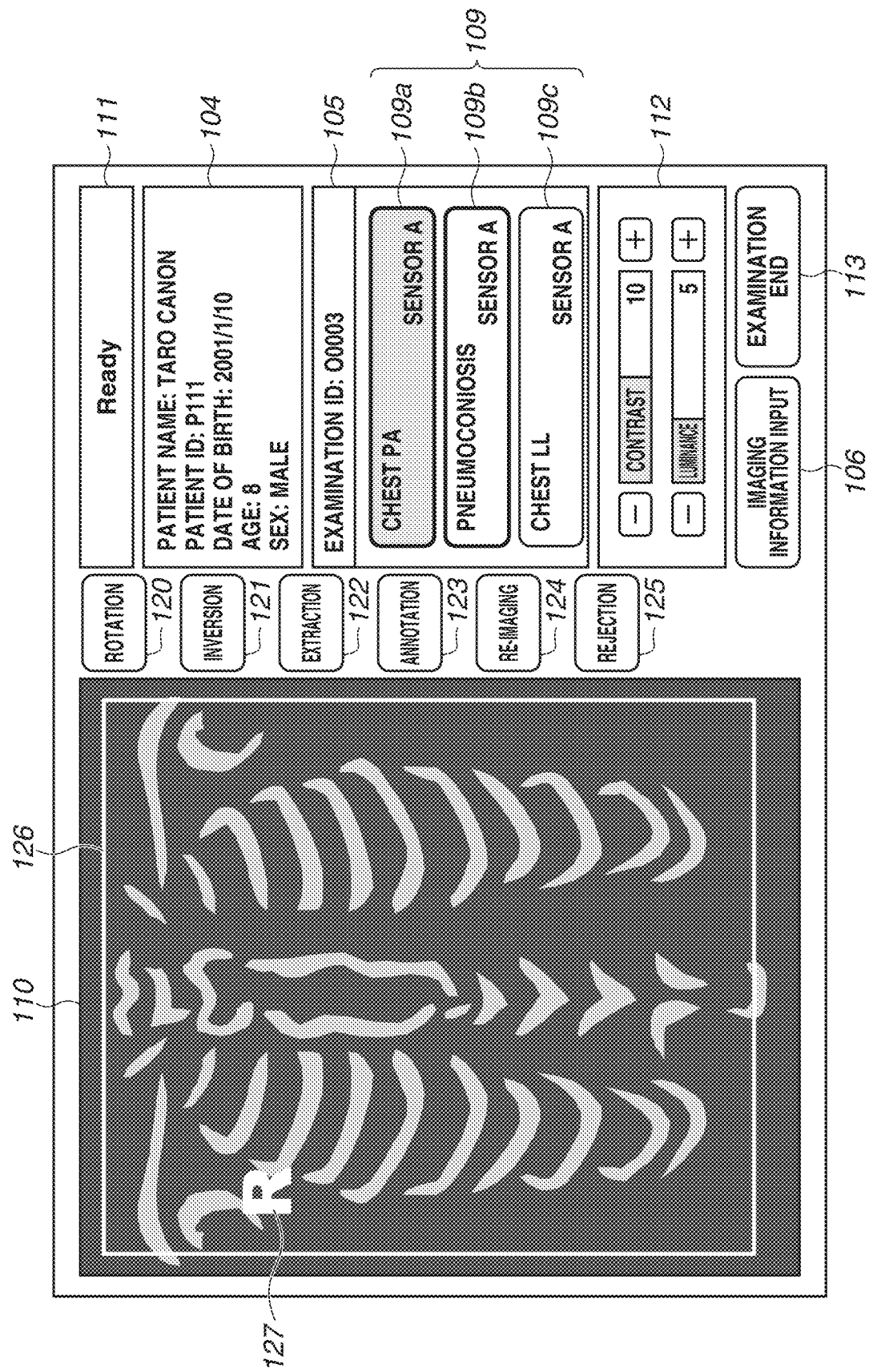
FIG. 4 is a diagram illustrating a display form of the radiographic system according to the exemplary embodiment.

FIG. 4 illustrates a display form for the display unit 2 of the radiographic system according to the present exemplary embodiment. FIG. 4 illustrates an imaging screen that is displayed on the display unit 2 after the examination to be performed is designated and start of the examination is instructed. As illustrated in FIG. 4, the display unit 2 displays a captured image display area 110, an examinee information display area 104, an examination information display area 105, an imaging protocol icon 109 (e.g., a chest PA icon 109a, a pneumoconiosis icon 109b, and a chest LL icon 109c) corresponding to an imaging protocol, and an image processing setting area 112. The examinee information display area 104 includes an examinee name, an examinee ID, a date of birth, an age, and a sex.

When the imaging screen is displayed, the imaging protocol icon 109a disposed at an uppermost part in the examination information display area 105 is selected by default. The control unit 5 of the radiographic apparatus 1 transmits the imaging condition (e.g., tube voltage, tube current, and irradiation time) set corresponding to the imaging protocol, to the radiation generation apparatus 4 accordingly. Further, the control unit 5 controls the radiation detection apparatus 7 based on the imaging method information to prepare for imaging.

After preparations for the imaging is completed, the radiographic apparatus 1 makes a transition to an imagable state. At this time, "Ready" message indicating that the apparatus is in the imagable state is displayed on a message area 111.

At this time, the display unit 2 highlights, based on a result of the determination by the determination unit 25, the imaging protocol icon belonging to the imaging method group same as the imaging protocol that has turned into the imagable state. Specifically, the display unit 2 highlights the pneumoconiosis icon 109b that belongs to the imaging method group same as the chest PA icon 109a in the imagable state. The highlight display of the icon indicates change of a display mode of the icon (e.g., color and frame of icon) for distinction from the other icons. The operator can perceive that there is the imaging protocol belonging to the imaging method group same as the imaging protocol that has turned into the imagable state.

Next, the operator checks the imaging method, and performs setting of the imaging and positioning of the examinee. After a series of imaging preparation is completed, the operator checks the imagable state with reference to the message area 111, and presses a radiation irradiation switch (not illustrated) of the radiation generation apparatus 4 that generates a radiation. The radiographic apparatus 1 then causes the radiation generation unit 8 to apply the radiation to the examinee (e.g., imaged region of examinee), and causes the radiation detection apparatus 7 to detect a radiation passed through the examinee. Thereby, the imaging of the radiographic image is performed.

After the imaging is completed, the control unit 5 of the radiographic apparatus 1 acquires the captured image from the radiation detection apparatus 7, and at the same time the image processing unit 22 performs the image processing on the radiographic image based on a predetermined image processing condition. The predetermined image processing condition is previously specified corresponding to the imaging method. In a case where the same examination includes the imaging protocol belonging to the imaging method group same as the imaging protocol, the imaging of which has been completed, the image processing unit 22 performs the image processing on the imaging protocol based on the above-described predetermined image processing condition.

An image displayed on the captured image display area 110 is changed through operation on the imaging protocol icon, the imaging of which has been completed. At the time when the imaging is completed, a radiographic image of the chest PA protocol corresponding to the chest PA icon 109a is displayed on the captured image display area 110. The operator can display a radiographic image of the pneumoconiosis protocol by operating the pneumoconiosis icon 109b.

After the image processing is completed, the radiographic apparatus 1 displays the image-processed captured image on the captured image display area 110. In order to change contrast or the like of the captured image, the operator operates a contrast icon, a luminance icon and the like provided in the image processing setting area 112.

Likewise, in order to change an extraction area of an output image, the operator operates, for example, an extraction icon 122, and an extraction frame 126 to designate a desired extraction area. In order to provide a character string as diagnosis information, the operator operates, for example, an annotation icon 123 to superimpose a character string illustrated as an annotation 127 on the image. In a case where a direction of the radiographic image is not suitable for diagnosis, geometrical conversion is performed with use of, for example, a rotation icon 120, and an inversion icon 121. In a case where the radiographic image is not suitable for diagnosis, setting for re-imaging or rejection is performed with use of, for example, a re-imaging icon 124, and a rejection icon 125. As described above, the operator can additionally edit the radiographic image displayed on the captured image display area 110.

The operator repeats the above-described procedure to perform imaging corresponding to all of the imaging protocol icons in the examination information display area 105. After all of the imaging is performed, the operator presses an examination end icon 113. Thereby, the series of examinations ends.

Figure 5:
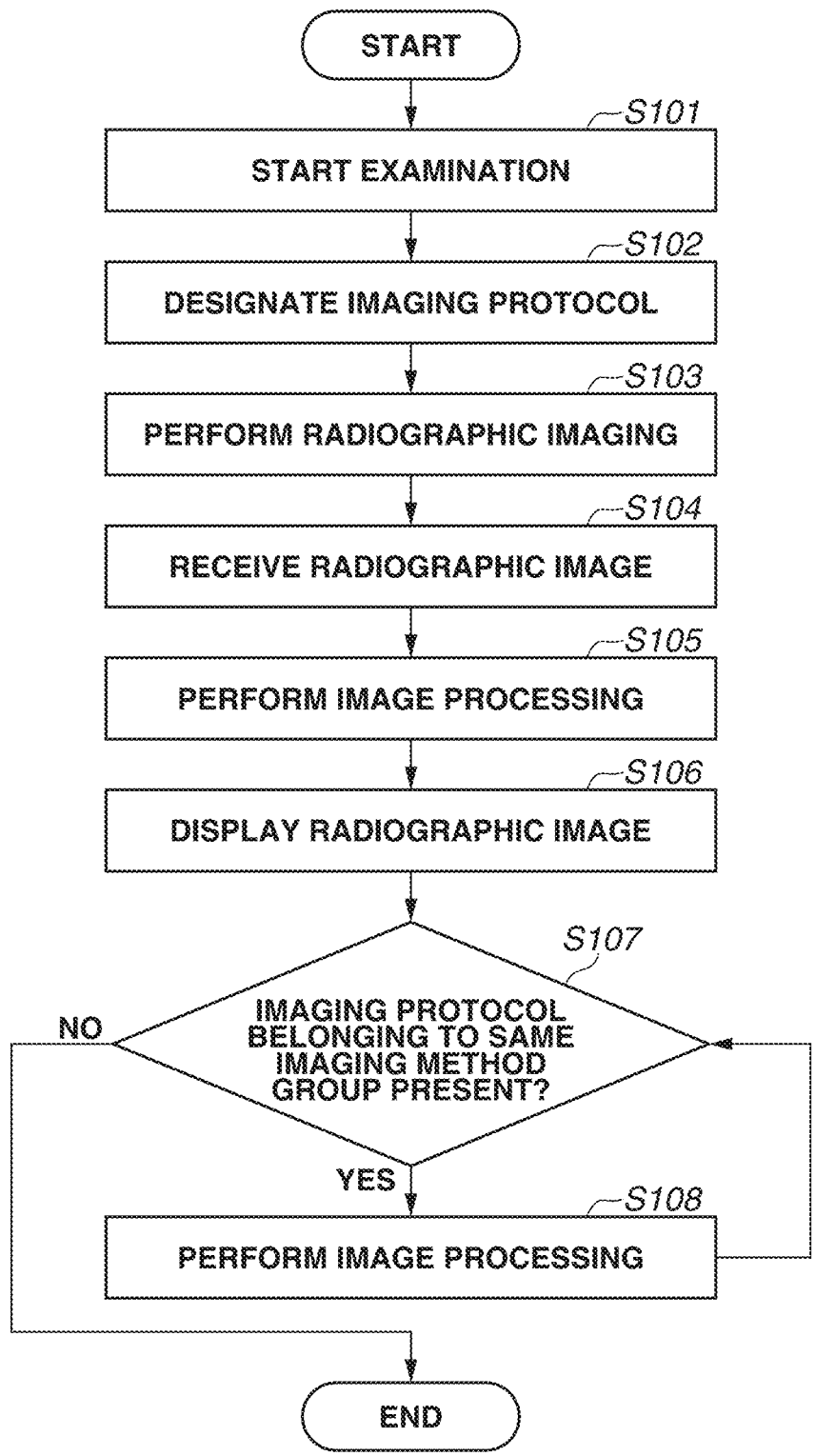
FIG. 5 is a flowchart illustrating operation by the radiographic system according to the exemplary embodiment.

Next, a procedure of imaging and application of the image processing is described with reference to a flowchart illustrated in FIG. 5.

First, in step S101, the operator creates an examination order to be performed through the operation unit 3, and instructs start of the examination. In a case where the examination order is received from the RIS 12, a list is displayed on the display unit 2, and the operator selects the examination order from the list.

In step S102, the control unit 5 displays the imaging screen as illustrated in FIG. 4 on the display unit 2. The operator operates the imaging protocol icon 109 to designate the imaging protocol. A top imaging protocol icon may be automatically designated in response to the instruction of the examination start.

In step S103, the operator sets the radiation generation apparatus 4 and the radiation detection apparatus 7 with respect to the examinee 10, to prepare for imaging. After the preparations for the imaging is completed, the operator presses the radiation irradiation switch of the radiation generation apparatus 4 that generates a radiation, to apply the radiation to the radiation detection apparatus 7. The radiation detection apparatus 7 that has detected the radiation generates a radiographic image.

In step S104, the imaging control unit 21 receives imaging execution notification from the radiation detection apparatus 7, and receives the generated radiographic image. The received radiographic image is associated with the performed imaging protocol by the examination management unit 24, and is stored into the storage unit 23.

In step S105, the imaging control unit 21 further causes the image processing unit 22 to perform the image processing on the received radiographic image. The image processing condition used at this time is previously set for the imaging protocol as illustrated, for example, in FIG. 3A and FIG. 3D. In step S106, the image-processed radiographic image is displayed on the display unit 2. Accordingly the series of flow relating to the imaging in step S103 is completed.

In step S107, the determination unit 25 determines whether the imaging protocol performed by the radiation detection apparatus 7 belongs to the imaging method group same as the imaging protocol stored in the storage unit 23, or determines whether the same examination under execution includes the imaging protocol belonging to the imaging method group same as the imaging protocol, the imaging of which has been performed.

In a case where there is the imaging protocol belonging to the same imaging method group (YES in step S107), the examination management unit 24 associates the imaging protocol and the radiographic image. Further, in step S108, the image processing unit 22 performs the image processing based on the imaging protocol belonging to the same imaging method group. The above-described processing is performed until there is no imaging protocol belonging to the same imaging method group. The image-processed radiographic image can be displayed on the display 2 through instruction with the imaging protocol icon 109.

As described above, according to the present exemplary embodiment, the radiographic system includes the storage unit 23 configured to store the plurality of imaging methods in association with the plurality of imaging protocols, the determination unit 25 configured to determine whether the imaging method of the imaging protocol associated with the examination order matches any of the plurality of imaging methods stored in the storage unit 23, and the image processing unit 22 configured to apply the image processing condition of the imaging protocol corresponding to the matching imaging method to the radiographic image captured based on the imaging protocol associated with the examination order in the case where the determination unit 25 determines that the imaging method matches. Accordingly, appropriately performing the image processing based on the imaging protocol associated with the examination order makes it possible to effectively perform the radiographic imaging.

Figure 6:
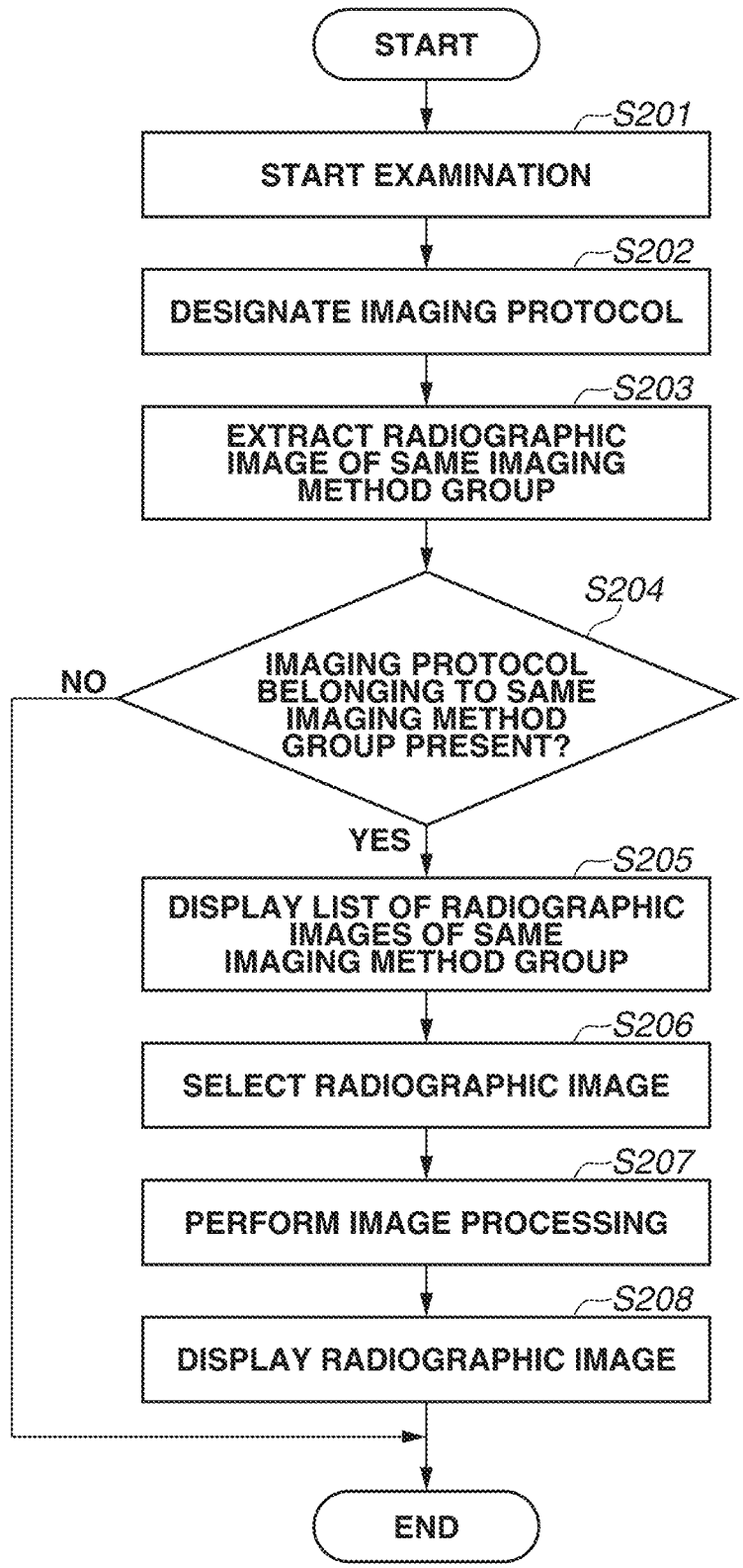
FIG. 6 is a flowchart illustrating operation by a radiographic system according to an exemplary embodiment.

A second exemplary embodiment of the radiographic system according to the present invention is described with reference to FIG. 6. In the first exemplary embodiment, the radiographic image acquired by the immediately-before imaging is applied to the imaging protocol belonging to the same imaging method group. In the second exemplary embodiment, the radiographic image of the imaging protocol belonging to the same imaging method group captured in a specified past period is applied.

Description of a configuration of the second exemplary embodiment is omitted because the configuration is similar to the configuration of the first exemplary embodiment. Operation of the radiographic system according to the present exemplary embodiment is described with reference to a flowchart illustrated in FIG. 6.

In step S201, the operator first starts the examination in a manner similar to step S101 according to the first exemplary embodiment.

In step S202, the operator operates the imaging protocol icon 109 to designate the imaging protocol.

In step S203, the examination management unit 24 extracts the imaging protocol of the same examinee stored in the storage unit 23. The imaging protocol to be extracted is limited to the imaging protocol, the imaging of which has been performed within a preset predetermined period from the day.

In step S204, the determination unit 25 determines whether the imaging protocol belonging to the imaging method group same as the imaging protocol designated in step S201 is included in the imaging protocols of the same examinee.

In a case where there are the imaging protocols belonging to the same imaging method group (YES in step S204), a list of the imaging protocols is displayed, in step S205, on the display unit 2.

In step S206, the operator selects the radiographic image from the list of the imaging protocols. For determination of selection, the imaging date, the imaging protocol name, a thumbnail image, and the like are preferably displayed in the list of the imaging protocols.

The examination management unit 24 stores the imaging protocol designated in step S202 and the radiographic image selected in step S206 in the storage unit 23 in association with each other.

In step S207, the imaging control unit 21 further causes the image processing unit 22 to perform the image processing on the selected radiographic image. The image processing previously set for the imaging protocol is performed as with step S105 according to the first exemplary embodiment.

In step S208, the image-processed radiographic image is displayed on the display unit 2.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-169616, filed Sep. 11, 2018, which is hereby incorporated by reference herein in its entirety.

What is claimed is:

1. A radiographic system, comprising:
a memory; and
one or more processor in communication with the memory to function as:
a storage unit configured to store a plurality of imaging methods and a plurality of imaging processing conditions in association with a plurality of imaging protocols;
a determination unit configured to determine whether there are imaging protocols for which imaging methods stored in the storage unit match each other among a plurality of imaging protocols associated with an examination order; and
an image processing unit configured to apply, in a case where the determination unit determines that there are imaging protocols for which the imaging methods match each other, the plurality of image processing conditions stored in the storage unit and corresponding to an imaging protocol when a radiographic image is captured based on the imaging protocol for which the imaging method matches, separately apply the plurality of image processing conditions stored in the storage unit and corresponding to the imaging protocol for which the imaging method matches and generates a plurality of radiographic images from the captured radiographic image.

2. The radiographic system according to claim 1, wherein the determination unit determines whether or not at least an imaged region and an imaging direction of the imaging method matches the imaged region and the imaging direction of the at least one imaging method.

3. The radiographic system according to claim 2, wherein the determination unit determines that the imaging methods are coincident in a case where the imaged region and the imaging direction of the imaging protocol associated with the examination order are respectively same as an imaged region and an imaging direction of any of the imaging protocols stored in the storage unit.

4. The radiographic system according to claim 1, further comprising a determination condition setting unit configured to set a determination condition used in the determination unit.

5. The radiographic system according to claim 4, wherein the determination condition setting unit sets the determination condition by adding a determination parameter in addition to an imaged region and an imaging direction.

6. The radiographic system according to claim 5, wherein the determination parameter is at least one of an imaging attitude, an imaging condition of a radiation in a radiation generation apparatus, and an image processing condition.

7. The radiographic system according to claim 1, wherein the determination unit determines whether the imaging protocol associated with the examination order belongs to an imaging method group same as the imaging protocols stored in the storage unit.

8. The radiographic system according to claim 1, further comprising a display unit configured to display the radiographic image, wherein the display unit highlights an icon corresponding to the imaging protocol of the matching imaging method determined by the determination unit.

9. A radiographic method, comprising:
storing a plurality of imaging methods and a plurality of image processing conditions in association with a plurality of imaging protocols;
determining whether there are imaging protocols for which stored imaging methods match each other among a plurality of imaging protocols associated with an examination order; and
applying, in a case where it is determined that there are imaging protocols for which the imaging methods match each other, the stored plurality of image processing conditions and corresponding to an imaging protocol when a radiographic image is captured based on the imaging protocol for which the imaging method matches, separately apply the stored plurality of image processing conditions and corresponding to the image protocol for which the imaging method matches and generates a plurality of radiographic images.

10. A non-transitory computer-readable storage medium that stores a program to cause a computer to execute a radiographic method, the radiographic method comprising:
storing a plurality of imaging methods and a plurality of image processing conditions in association with a plurality of imaging protocols;
determining whether there are imaging protocols for which stored imaging methods match each other among a plurality of imaging protocols associated with an examination order; and
applying, in a case where it is determined that there are imaging protocols for which the imaging methods match each other, the stored plurality of image processing conditions corresponding to an imaging protocol when a radiographic image is captured based on the imaging protocol for which the imaging method matches, separately apply the stored plurality of image processing conditions and corresponding to the imaging method matches and generates a plurality of radiographic images.

* * * * *